(12) United States Patent
Fukuoka et al.

(10) Patent No.: US 8,094,186 B2
(45) Date of Patent: Jan. 10, 2012

(54) SKIN CONDITION DIAGNOSIS SYSTEM AND BEAUTY COUNSELING SYSTEM

(75) Inventors: Masakazu Fukuoka, Chuo-ku (JP); Masami Hamaguchi, Chuo-ku (JP); Takeyoshi Kurihara, Chuo-ku (JP); Hiroyuki Ohnishi, Chuo-ku (JP); Yukiko Himuro, Chuo-ku (JP); Ruriko Takano, Chuo-ku (JP); Megumi Mizugaki, Chuo-ku (JP); Yuichi Ibaraki, Chuo-ku (JP); Kiyoshi Kawasaki, Chuo-ku (JP)

(73) Assignee: Shiseido Company, Ltd., Tokyo (JP)

( * ) Notice: Subject to any disclaimer, the term of this patent is extended or adjusted under 35 U.S.C. 154(b) by 1021 days.

(21) Appl. No.: 11/577,773

(22) PCT Filed: Oct. 24, 2005

(86) PCT No.: PCT/JP2005/019524
§ 371 (c)(1),
(2), (4) Date: Apr. 23, 2007

(87) PCT Pub. No.: WO2006/043702
PCT Pub. Date: Apr. 27, 2006

(65) Prior Publication Data
US 2009/0201365 A1    Aug. 13, 2009

(30) Foreign Application Priority Data

Oct. 22, 2004  (JP) ................... 2004-307892

(51) Int. Cl.
*A61B 5/00* (2006.01)
(52) U.S. Cl. ............... 348/77; 600/306; 382/128
(58) Field of Classification Search ............ 348/77; 600/306; 382/128
See application file for complete search history.

(56) References Cited

U.S. PATENT DOCUMENTS

| 5,799,111 A * | 8/1998 | Guissin .......... 382/254 |
| 6,571,003 B1 * | 5/2003 | Hillebrand et al. ....... 382/118 |
| 2004/0028263 A1 * | 2/2004 | Sakamoto ........ 382/128 |
| 2004/0122299 A1 * | 6/2004 | Nakata ........... 600/306 |

* cited by examiner

*Primary Examiner* — Kenneth R Coulter
(74) *Attorney, Agent, or Firm* — Cozen O'Connor

(57) ABSTRACT

A data collection system is connected to a data analysis system that carries out analysis processing based on data collected by the data collection system via communication. The data collection system includes collection-side communication, image capturing for capturing an ultra-high resolution digital image that allows an analysis of a skin texture condition, collection-side image data compression for compressing image data by a high compression method with block noises suppressed, and collection-side data display. The data analysis system includes analysis side communication, data analysis for analyzing image data, and analysis-side data compression for compressing the data by a high compression method with block noises suppressed.

16 Claims, 16 Drawing Sheets

Fig. 8

| | Diagnostic item | Coeffecient value | Medium item | Coeffecient value | |
|---|---|---|---|---|---|
| B1 | Brightness (whiteness) | b1 | | | |
| B2 | Color | b2 | | | |
| B3 | Dullness of whole face | b3 | | | |
| B4 | Dullness of lips | b4 | C1 Color | c1 | |
| B5 | Highly visible spots and freckles | b5 | | | |
| B6 | Color irregularity of portion | b6 | | | |
| B7 | Color irregularity of cheek | b7 | | | |
| B8 | Dark circles | b8 | | | |
| B9 | Fine skin | b9 | | | |
| B10 | Smooth skin | b10 | | | |
| B11 | Dry skin | b11 | | | |
| B12 | Radiant skin | b12 | C2 Irregularity | c2 | |
| B13 | Nose pore | b13 | | | A Skin condition |
| B14 | Cheek pore | b14 | | | |
| B15 | Pimples and their marks | b15 | | | |
| B16 | Supple skin | b16 | | | |
| B17 | Slacks of upper lid | b17 | | | |
| B18 | Undereye bag | b18 | | | |
| B19 | Sagging cheek | b19 | | | |
| B20 | Sagging face line | b20 | | | |
| B21 | Sagging neck | b21 | | | |
| B22 | Wrinkles on the brow | b22 | C3 Vitality | c3 | |
| B23 | Scowl lines | b23 | | | |
| B24 | Creases around the eye | b24 | | | |
| B25 | Wrinkles of cheek | b25 | | | |
| B26 | Smile lines | b26 | | | |
| B27 | Wrinkles of lips | b27 | | | |
| B28 | Neck wrinkles | b28 | | | |

Fig. 9

$$\{C1\} = \{B1\} \times b1 + \{B2\} \times b2 + \{B3\} \times b3 + \{B4\} \times b4$$
$$+ \{B5\} \times b5 + \{B6\} \times b6 + \{B7\} \times b7 + \{B8\} \times b8 \quad \cdots (1)$$

$$\{C2\} = \{B9\} \times b9 + \{B10\} \times b10 + \{B11\} \times b11$$
$$+ \{B12\} \times b12 + \{B13\} \times b13 + \{B14\} \times b14 + \{B15\} \times b15 \quad \cdots (2)$$

$$\{C3\} = \{B16\} \times b16 + \{B17\} \times b17 + \{B18\} \times b18$$
$$+ \{B19\} \times b19 + \{B20\} \times b20 + \{B21\} \times b21$$
$$+ \{B22\} \times b22 + \{B23\} \times b23 + \{b24\} \times b24$$
$$+ \{B25\} \times b25 + \{B26\} \times b26 + \{B27\} \times b27 + \{B28\} \times b28 \quad \cdots (3)$$

$$\{A\} = \{C1\} \times c1 + \{C2\} \times c2 + \{C3\} \times c3 \quad \cdots (4)$$

Fig. 13

| Medium Item | | Diagnostic Item |
|---|---|---|
| C1 Whitening | B1 | Brightness (whiteness) |
| | B2 | Color |
| | B3 | Dullness of whole face |
| | B4 | Dullness of lips |
| | B5 | Highly visible spots and freckles |
| | B6 | Color irregularity of portion |
| | B7 | Color irregularity of cheek |
| | B8 | Dark circles |
| C2 Blood circulation | | B2, B3, B4, B6, B7, B8, B12 |
| C3 Moisture retention | | B9, B10, B11, B12, B15, B16 |
| C4 Astringency | | B13, B14 |
| C5 Sebum and horny plug | | B13, B14, B15 |
| C6 Sagging | | B14, B16, B17, B18, B19, B20, B21, B25, B26, B28 |
| C7 Dry wrinkles | | B24, B26, B27 |
| C8 Aged wrinkles | | B22, B23, B24, B25, B26, B28 |

Fig. 16

SKIN CONDITION DIAGNOSIS SYSTEM AND BEAUTY COUNSELING SYSTEM

TECHNICAL FIELD

The present invention relates to a system which diagnoses a skin condition of a customer, a subject, at the store such as cosmetics stores.

BACKGROUND ART

It has been common practice to magnify and observe the skin of a customer by use of a microscope and diagnose its skin condition at the store where sales of cosmetics are performed.

It has also been practiced that a microscope connected to an image processing device such as a personal computer is applied to a specific portion of the face, its enlarged image is displayed on a display unit, and the image processing device analyzes the image captured from the microscope to quantitatively evaluate the skin condition such as a texture condition, etc.

In the stores which have this kind of equipment, salespersons select products which are suited for the customer by use of the diagnosis results of the skin condition, and supervise the directions for use of the products.

DISCLOSURE OF INVENTION

Problems to be Solved by the Invention

However, because the area on the face which can be captured by the microscope at one time is small, diagnosis results based on the captured image deal with merely local information. For example, even when a fleck condition of the cheek is measured, data on only a small part of the total area of the cheek is captured. For this reason, unless the site is in the condition which represents the whole cheek, it cannot be said that the cheek condition is diagnosed. For example, in the case where a fleck is only present at the place where the microscope is applied, the diagnostic results which indicate the whole cheek condition cannot be obtained.

Therefore, in order to obtain highly reliable results, images of as many portions as possible should be captured and analyzed. However, it takes time and labor to repeatedly apply the microscope to the customer's face and capture images in order to capture, for example, the whole cheek or whole forehead.

Even if the range is limited to a certain range, such as cheek, forehead, etc., it is not realistic to capture a large number of places by the microscope and diagnose the condition of the whole face.

In addition, in order to capture a large volume of information and analyze all of them, long processing time is required. It is only a few minutes that the customer can wait without doing anything until images and other customer information are all inputted at the store and the analysis results are outputted. In order to obtain results in this period, a large-scale computer with high processing speed is essential. However, it is nearly impossible to install such a large-size computer at each store.

However, there is also a problem that a person with considerable experience is required to specify an image capturing point that represents the condition of a portion with a certain degree of width and apply the microscope to the portion to capture images.

Further, in a diagnostic unit using a microscope, it is possible to display an enlarged image of a captured portion but it is unable to specity to where of the customer's face the enlarged image corresponds, that is, it is unable to identify its exact position on the face. Consequently, there is also a problem that customers are unable to identify which part of their faces the enlarged image corresponds to and are unable to realize even if the diagnostic results are presented.

Moreover, there is still another problem in that the operation for applying a microscope to the face and capture analyzable images requires a knack to apply the microscope, and it is a difficult operation for a beginner, who is not accustomed to the operation.

It is an objective of the present invention to provide a system for diagnosing a skin condition of the face of a customer, a subject, at the store, whose operation at the time of diagnosis is made simple to allow even a beginner to perform diagnosis, and the precision of whose diagnostic results is improved.

Means for Solving the Problems

A first invention is a skin condition diagnosis system including a data collection system and a data analysis system that carries out analysis processing based on data collected by the data collection system, both of which are connected via communication means, characterized in that the data collection system includes: collection-side communication means for transmitting and receiving data to and from the data analysis system; image capturing means for capturing an ultra-high resolution digital image of such a level as to allow an analysis of a skin texture condition; collection-side image data compression means for compressing image data by a high-compression method with block noises suppressed; and collection-side data display means, the data analysis system includes: analysis-side communication means for transmitting and receiving data to and from the data collection means; data analysis means for analyzing image data; analysis-side image data compression means for compressing the image data by a high-compression method with block noises suppressed; and analysis-side data storage means for storing analysis results by the data analysis means, the image capturing means captures a whole face image of a subject as an ultra-high resolution digital image, the collection-side image data compression means has a function of compressing the whole face image to create compressed image data and transmitting the data to the data analysis system via the collection-side communication means, the data analysis means has a function of receiving the compressed image data via the analysis-side communication means, analyzing the skin condition of the subject on the basis of the received compressed image data, creating visual information which reflects the analysis results on the whole face image, and outputting the visual information as a diagnosis result, the analysis-side image data compression means compresses the diagnosis result outputted from the data analysis means to create compressed image data, and transmits the compressed image data to the data collection system via the analysis-side communication means, and the collection-side data display means has a function of displaying the diagnosis result transmitted from the analysis-side communication means.

In a system that receives compressed image data transmitted between the data collection system and the data analysis system, the compressed image data is decompressed at the time of processing the data.

A second invention is, on the premise of the first invention, characterized in that the data analysis system further includes storage means for storing a plurality of diagnostic items concerning the skin condition, and that the data analysis means has a function of analyzing the skin condition for each of the diagnostic items from whole face image data, computing grades on the basis of the analysis results, and reflecting evaluation results corresponding to the grades to the whole face image.

A third invention is, on the premise of the second invention, characterized in that the storage means classifies the plurality of diagnostic items into at least two or more kinds of medium items and stores them, and simultaneously stores the medium items and the diagnostic items in such a manner as to be associated with coefficient values, and that the data analysis means aggregates scores of all the diagnostic items, which are obtained by multiplying the computed grade of each diagnosis item by the coefficient value corresponding to the diagnosis item, for each medium item to compute a medium item grade, multiplies the medium item grade by a coefficient value corresponding to the medium item, and aggregates the multiplied scores to compute the grade of the skin condition.

A fourth invention is, on the premise of the third invention, characterized in that the coefficient value is a value computed by analyzing a relationship between a visual grade of the skin condition visually determined and the grade of each diagnosis hem computed by the data analysis means.

A fifth invention is, on the premise of the third and fourth inventions, characterized in that the data analysis means has a function of creating display data for displaying the computed grade and the coefficient value corresponding to the item on the same screen.

A sixth invention is, on the premise of the first and fifth inventions, characterized in that the data analysis means executes: a process for specifying a constituent element of the face from a whole face image received from the data collection system; a process for specifying a diagnostic items; a process for specifying a diagnosed portion on the whole face image that conforms to the specified diagnostic item on the basis of the constituent element of the face; and a process for analyzing image characteristics which appear in accordance with the skin condition that corresponds to the diagnostic item in the diagnosed portion.

A seventh invention is a skin condition diagnosis system including a data collection system and a data analysis system that carries out analysis processing based on data collected by the data collection system, both of which are connected via communication means, characterized in that the data collection system includes: collection-side communication means for transmitting and receiving data to and from the data analysis system; image capturing means for capturing an ultra-high resolution digital image that allows an analysis of a skin texture condition; collection-side image data compression means for compressing image data by a high-compression method with block noises suppressed; and collection-side data display means, the data analysis system includes: analysis-side communication means for transmitting and receiving data to and from the data collection means; data analysis means for analyzing image data; analysis-side image data compression means for compressing the image data by a high-compression method with block noises suppressed; analysis-side data storage means for storing analysis results by the data analysis means; and change trend storage means for storing trends of changes with time that are compatible with preset skin conditions and face shape patterns, the image capturing means captures a whole face image of a subject as an ultra-high resolution digital image, the collection-side image data compression means has a function of compressing the whole face image to create compressed image data and transmitting the data to the data analysis system via the collection-side communication means, the data analysis means has: a function of receiving the compressed image data via the analysis-side communication means, analyzing the skin condition of the subject on the basis of the received compressed image data, creating visual information which reflects the analysis results on the whole face image, and outputting the visual information as a diagnosis result; a function of specifying the pattern from the skin condition and the face shape of the subject, and simultaneously specifying a change trend corresponding to the pattern from the data stored in the change trend storage means; and a function of predicting the future skin condition and face shape of the subject on the basis of the specified change trend and reflecting the prediction result to the whole face image to output it as a predicted future face image, the analysis-side image data compression means compresses the predicted future face image outputted from the data analysis means to create compressed image data, and transmits the compressed image data to the data collection system via the analysis-side communication means, and the collection-side data display means has a function of displaying the predicted future face image transmitted from the analysis-side communication means.

A counseling system for beauty, which is an eighth invention, includes a data collection system and a data analysis system that carries out analysis processing based on data collected by the data collection system, both of which are connected via communication means, characterized in that the data collection system includes: collection-side communication means for transmitting and receiving data to and from the data analysis system; image capturing means for capturing an ultra-high resolution digital image of such a level as to allow an analysis of a skin texture condition; collection-side image data compression means for compressing image data by a high-compression method with block noises suppressed; and collection-side data display means, the data analysis system includes: analysis-side communication means for transmitting and receiving data to and from the data collection means; data analysis means for analyzing image data; analysis-side image data compression means for compressing the image data by a high-compression method with block noises suppressed; analysis-side data storage means for storing analysis results by the data analysis means; and beauty information storage means for storing beauty information such as cosmetic information, the image capturing means captures a whole face image of a subject as an ultra-high resolution digital image, the collection-side image data compression means has a function of compressing the whole face image to create compressed image data and transmitting the data to the data analysis system via the collection-side communication means, the data analysis means has: a function of receiving the compressed image data via the analysis-side communication means, analyzing the skin condition of the subject on the basis of the received compressed image data creating visual information which reflects the analysis results on the whole face image, and outputting the visual information as a diagnosis result; and a function of extracting and outputting beauty information suited for the subject from the beauty information storage means on the basis of the analysis results, the analysis-side image data compression means compresses the diagnosis result outputted from the data analysis means to create compressed image data, and transmits the compressed image data together with the extracted beauty information to the data collection system via the analysis-side communication means, and the collection-side data display means has a function of displaying the diagnosis result and beauty information transmitted from the analysis-side communication means.

EFFECT OF THE INVENTION

According to the first to eighth inventions, because a whole face image with ultra-high definition is transmitted in a short time, a data analysis system which can make a high-precision diagnosis can be installed separately from a data collection system.

By separating a large-size processing device that performs a high-precision analysis from a data collection system, a small-size data collection system can be installed at many stores, etc.

Because it is possible to capture a whole face image by an easy operation to use a camera on the data collection system side of stores, etc., even a beginner can capture a whole face image of a customer as compared to the case of using a conventional microscope.

As a result, more highly accurate diagnosis results can be easily obtained.

In addition, because the diagnostic results are visually expressed on the whole face image, subjects such as customers, etc. of cosmetic stores could easily accept the diagnosis results.

Furthermore, because data concerning the skin condition of the whole face can be simultaneously captured by the whole face image, the skin condition of the whole face can be comprehensively evaluated. If the data of the whole face is unable to be captured simultaneously, the time of capturing the data differs depending on places. On the other hand, since the skin condition varies with time, it is impossible to evaluate the whole face under the condition of the same time if there is any time difference in capturing the data depending on places. Consequently, when the skin condition of the whole face is comprehensively evaluated, correct evaluation results may not be obtained. However, capturing the whole face image at one time as is the case with the present invention can eliminate this kind of concerns.

According to the second to fourth inventions, the skin condition can be comprehensively evaluated and displayed.

In particular, according to the fourth invention, the evaluation results of the skin condition to look at, that is, the visual skin condition can be computed.

According to the fifth invention, the degree of contribution of each item to comprehensive evaluation results of the skin condition can be identified. Consequently, it can tell by just looking which diagnostic items should be improved in order to improve the comprehensive evaluation results of the skin condition.

According to the sixth invention, a portion that should be analyzed on the image can be specified in accordance with the diagnostic items.

According to the seventh invention, a predicted future face image which predicts the future can be outputted on the basis of the skin condition of the subject. Making the best of the predicted future face image, appropriate advice could be given on beauty.

According to the eighth invention, even a person who has no experience can give counseling on beauty at the store, etc.

BEST MODE FOR CARRYING OUT THE INVENTION

A first embodiment of the present invention will be described with reference to FIGS. 1 and 2.

In a system of the first embodiment, data collection systems 1 installed, respectively, in a plurality of stores are connected to a data analysis system 11 installed at a control center via a communication network N such as Internet. The location of the data collection system 1 is not limited to a store but in the following embodiments, the data collection system 1 is installed in stores such as cosmetic stores, etc.

In the skin condition diagnosis system, data necessary for diagnosis is transmitted from the data collection system 1 to the data analysis system 11, results obtained by analysis of the data analysis system 11 are transmitted to the data collection system 1, and the analysis results are displayed in a display unit 3.

As shown in FIG. 1, the data collection system 1 comprises a photographing unit 2 which is image capturing means for capturing an ultra-high definition digital image of the invention, the display unit 3 that displays data, an input unit 4, such as a keyboard or a card reader, for inputting customer information, etc., a storage unit 5 that stores data therein a processing unit 6, an output unit 8 that outputs data, and a transmitting and receiving unit 7 that is collection-side communication means of the present invention to carry out communication with the data analysis system 11 via the communication network N.

All the data collection systems 1 installed in the stores have the same configuration.

The photographing unit 2 is a digital camera which takes pictures of a whole face of a customer, a subject, as digital images with ultra-high definition which enable an analysis of a skin texture condition. The ultra-high definition which enables the analysis of the skin texture condition means that there is provided resolution of such a level as to read fine line of 30 µm in width, and for example, it is the level equivalent to or higher than the level of a microscope at 50 power on a current 14-inch monitor. The larger the number of pixels of an image to be captured, the easier is the analysis of the texture condition. Specifically, 20,000,000 pixels or more are required, and 40,000,000 pixels or more are preferable.

The display unit 3 is a display unit that can display ultra-high definition digital images, and the output unit 8 is a printer, etc. for outputting the analysis results and other data returned from the data analysis system 11.

The processing unit 6 has a function of processing customer data inputted from the input unit 4 and image data inputted from the photographing unit 2, storing the data in the storage unit 5, and transmitting the data to the data analysis system 11 via the transmitting and receiving unit 7.

Examples of the data processing function of the processing unit 6 include a function of compressing ultra-high definition images inputted from the photographing unit 2. This compression method is a high compression method with block noises suppressed.

The compression method with block noises suppressed is a method which does not impair continuity of lines existent in an original image even when compressed image data is decompressed, and is the best suited method for analyzing the skin texture condition. Examples of software that achieves this kind of compression method include "MrSID" available from Celartem Technology Inc., etc.

A compression rate of high compression is one that can achieve a communication speed of returning the analysis results from the data analysis system within a few minutes after necessary data is inputted on the store side, and is about one twentieth.

For the compression method, various kinds of software already commercially available can be utilized. To the collection-side processing unit 6, these pieces of software are set to compress image data.

That is, the collection-side processing unit 6 configures collection-side image data compression means of the invention.

On the other hand, the data analysis system 11 is equipped with a transmitting and receiving unit 12 that is analysis-side communication means for performing communication with the data collection system 1, a central processing unit 13 which corresponds to toe data analysis means and the analysis-side image data compression means, a storage unit 14, and various databases 15 to 19.

The storage unit 14 is a storage unit which stores the data transmitted from the data collection system 1 and stores the analysis results analyzed by the central processing unit 13. The databases 15 to 19 are databases having stored therein data necessary for an analysis processing when a data analysis of the central processing unit 13 later discussed in detail.

Examples of the database include customer database 15 having stored therein customer information transmitted from a plurality of data collection systems 1 connected to the control center, face image database 16 having stored therein customer face images, skin judgment criteria database 17 having stored therein criteria data when the skin condition is judged, skin-care database 18 having stored therein skin-care methods that correspond to skin characteristics, and product information database 19 having stored therein information on products which each store handles.

The criteria data stored in the skin judgment criteria database 17 is the criteria for substituting a level value of each skin condition for results of an image analysis performed for each diagnosis item. For example, in order to evaluate brightness (whiteness) of a whole face, the brilliance is measured from a face image, and a skin brightness level is determined by the measured value. The skin brightness level which is made equivalent to the image brilliance is the criteria data.

A function of image data compression possessed by the central processing unit 13 is same as the compression function of the collection-side processing unit 6, and the image data can be compressed by the high compression method with block noises suppressed.

Now, description will be made on a procedure to diagnose a skin condition of a customer who visits a store in which the data collection system 1 is installed.

In this part of the section, an example of comprehensively diagnosing the skin condition of the customer's face, for example, whether the skin has any problems such as dry skin, etc. will be discussed.

First, at the store, a person in charge captures whole face data of the customer using the photographing unit 2. Specifically, using a digital camera for ultra-high definition, the customer's face is photographed. At the time of photographing, a clearly focused whole face on camera must be captured. Since it is something that everyone can do to take pictures by use of a digital camera, and it is not particularly difficult to capture analyzable images if contrivances are made to the customer position, lighting conditions, and others. As compared to the case in which images are captured by a microscope, the operation is simple and is the work which even a beginner can do.

When a whole face image is captured from the photographing unit 2 as described above, the processing unit 6 compresses the image and transmits it to the data analysis system 11 via the transmitting and receiving unit 7 as compressed image data.

In the data analysis system 11, the central processing unit 13 receives the compressed image data via the transmitting and receiving unit 12 and analyzes the data after decompression.

With reference to FIG. 2, the analysis procedure will be described as follows.

The central processing unit 13 decompresses the compressed image data received and creates a whole face image. FIG. 2 shows the created whole face image 21. Based on the whole face image 21, a skin diagnosis is performed.

First, the central processing unit 13 recognizes a skin color of the whole face image 21, specifies a face contour on the basis of it, applies characteristic point data of each face part, such as eyes, nose, mouth, etc., which are constituent elements of the face stored in advance, and specifies the positions of the face parts in the whole face image 21.

Next, as shown in FIG. 3, an analysis portion 22 is determined based on the information of the face parts. The analysis portion 22 may be set to the whole face or may be set to a specific area, for example, to areas such as a cheek or tail of the eye in accordance with diagnostic items. The diagnostic items mean the items of the skin condition which is analyzed and judged from images in this system. Specifically they are items including wrinkles, dry skin, etc.

For example, to diagnose dry skin, a cheek which is likely to lose moisture is set in advance to the analysis portion, or to diagnose wrinkles, a tail of the eye and both corners of a mouth are set in advance to the analysis portion.

In the first embodiment, in order to diagnose the skin condition of the whole face, a plurality of diagnostic items are set in advance and the diagnosis is performed on all of them. For the determined analysis portions, data analysis is performed for each diagnostic item to obtain analysis results.

There are items to be analyzed, such as a texture condition, a pore shape and size, etc. and analysis procedure for each diagnostic item, such as wrinkles, dry skin, spots, and others. These analysis items and procedures are set in the analysis program of the central processing unit 13 in advance. The analysis is an image analysis processing of, for example, lightness, hue, and color distribution of the required portions that conform to the diagnosis items in the whole face image data captured on the side of the data collection system 1. For example, in the case where skin brightness (whiteness) is evaluated, lightness is measured from the whole image data, and in the case where a color is evaluated, a hue is evaluated from the whole image data, and all are compared to the criteria data to determine the grade or level value of the skin brightness.

Spots and dark circles are analyzed on the basis of the analysis data, such as portions with a concentration exceeding a reference value, and its density and area. Also for texture and wrinkles, by specifying a portion where dark portions are continued in the form of a line, texture and wrinkles are specified. By comparing the measured values such as its darkness, size, distribution, etc. to the reference data, the evaluation results are outputted.

Furthermore, among the diagnostic items, there are diagnostic items which are related to other diagnostic items. For example, dry skin is greatly related to the texture condition. Thus, in the case of the diagnosis, the texture condition of the analysis portion that corresponds to the diagnosis of dry skin is analyzed and the numerically converted texture condition is obtained. The value is compared to the criteria data of dry skin of the skin judgment criteria database 17, and the dry skin condition of the customer is determined.

For all the diagnostic items, the central processing unit 13 performs an image analysis of lightness, color, concentration, line arrangement, etc. of the required portion, in accordance with the analysis items for each diagnosis item. The analysis results of each analysis item are compared to the criteria data of the skin judgment criteria database 17, and the skin condition of the customer is judged for each diagnostic item.

When the skin condition is judged from the analysis results of all the items to be diagnosed, the central processing unit 13 creates image information with the diagnosis results reflected on the whole face image 21 as shown in FIG. 4.

That is, the central processing unit 13 creates the diagnosis results image data for displaying a portion 23 where wrinkles at the tail end of the eye are generated and a portion 24 where dry skin of the cheek is generated on the whole face image 21 by distinguishing them by using different colors as shown in FIG. 4.

The central processing unit 13 highly compresses the diagnosis result image data that indicate the diagnosis results by the compression method with block noises suppressed, and transmits them to the data collection system 1 via the transmitting and receiving unit 12.

In the data collection system 1 the received data is displayed on the display unit 3. On the display unit 3, as shown in FIG. 4, a screen with the skin conditions exhibited by distinguishing them by using different colors appears on the whole face image 21 of the customer.

As shown in FIG. 5, it is also possible to display the skin condition level obtained in the central processing unit 13 on the display unit 3 together with the whole face image 21 by a graph 30. The graph 30 shows the degree of the skin condition level for each diagnostic items including wrinkles as shown in FIG. 6.

However, the skin condition level may be displayed not by the graph 30 but by colors on the whole face image 21. For example, it is also possible to display the dry skin level by the color density used for indicating the dry skin areas.

By visually expressing the diagnostic results on the whole face image 21 in this way, the customer can know as much about his/her skin condition, and on the store side as well, the sales person is able to convince the customer more easily of hi/her skin condition.

Furthermore, as shown in FIG. 7, in the data collection system 1, selecting a specific position in the whole face image 21 displayed by a mouse pointer 31, etc. can display its enlarged image on an enlarged image display area 32.

The image displayed on the enlarged image display area 32 is the image based on the ultra-high definition image captured from the photographing unit 2 and is of such a level that the texture condition can be accurately recognized.

The reason why the skin condition can be diagnosed in accordance with the ultra-high definition whole face image at a realistic speed is attributed to the processing time shortened by allowing the data analysis system 11 of the control center with high processing capabilities to perform an actual analysis processing as well as to the communication time shortened by sending and transmitting image data after highly compressing.

It is meaningless if image data is deteriorated and the analysis accuracy of the skin condition is degraded by compressing the image data. However, the system of the present invention adopts the compression method which suppresses block noises to allow the image data to be compressed with the continuity of lines preserved, which is extremely important for skin analysis. Therefore, there is no concern of degrading the analysis accuracy by compression.

In the first embodiment, the skin condition of the whole face of the customer is checked but it may be allowed to analyze the diagnostic items only that the customer concerns, for example, a problem area of the skin, etc.

In this case, the problem area of the skin of the customer is inputted from the input unit 4 of the data collection system 1 and is transmitted to the data analysis system 11. In the data analysis system 11, the central processing unit 13 specifies the diagnostic item that corresponds to the problem area received, performs a data analysis by the procedure same as that of the first embodiment and outputs the diagnostic results.

Also in this case, on the display unit 3 of the data collection system 1, a portion corresponding to the problem area can be displayed with a specific color assigned to the portion on the customer's whole face image. In addition, the degree of skin damage can be shown by graph and score.

A second embodiment shown in FIGS. 8 to 10 is an example not only to display the skin condition concerning individual diagnostic items, as is the case with the first embodiment, but also to compute the comprehensive grade of the skin condition by aggregating these analysis results.

However, this second embodiment has the general system configuration same as that of the first embodiment shown in FIG. 1. Consequently, FIG. 1 is referred to discuss the second embodiment.

The comprehensive skin condition to be evaluated in the second embodiment is the skin condition which affects the appearance and is the beauty of the skin.

Because the procedure for producing diagnostic results from image analysis for individual diagnostic items and the function of displaying the diagnostic results on the customer's whole face image in the system of the second embodiment are same as those of the first embodiment, the description thereof will be omitted. A description will be made with primary emphasis placed on the function of computing the comprehensive grade of the skin condition.

In this system, as shown in FIG. 8, diagnostic items B1 to B28 are classified into three medium items, color C1, irregularity C2, and vitality C3, and the table in which the coefficient value has one to one correspondence to relevant items is stored in the skin judgment criteria database 17 shown in FIG. 1. That is, relevant coefficient values b1 to b28 have one to one correspondence to the diagnostic items B1 to B28, and relevant coefficient values C1 to C3 establish correspondence to the medium items C1 to C3, respectively.

The medium items C1 to C3 are elements involved with the skin condition A, and the condition that integrates these medium items is defined as the comprehensive skin condition A. Each of the medium items C1 to C3 generalizes the diagnostic results of the diagnostic items B1 to B28, which are classified into the medium items. Accordingly, diagnostic items related to the skin color such as complexion establish correspondence to the color C1 of the medium item, and diagnostic items related to irregularities of the skin surface have one to one correspondence to the irregularity C2. Furthermore, the vitality C3 is also the item related to the skin surface condition, to which diagnostic items which vary in accordance with aging primarily establish correspondence.

The coefficient values b1 to b28 of the diagnostic items B1 to B28 are numerical values that indicate the degree of contribution which the diagnostic items make to the classified medium items. The coefficient values c1 to c3 of the medium items C1 to C3 are numerical values that indicate the degree of contribution which these medium items C1 to C3 make to the skin condition A. The degree of contribution which brightness (whiteness) B1 makes to the color C1 of the medium item is the coefficient value b1, and the degree of contribution of color B2 is the coefficient value b2. This means that, for example, when the coefficient value b1 is greater than the coefficient value b2, the brightness (whiteness) B1 makes greater contribution to the visual skin condition A than the color B2.

As described in the first embodiment, the central processing unit 13 can perform diagnosis by analyzing the whole face image data of the customer, the subject, with respect to each of the diagnostic items B1 to B28, and can express the evaluation results in grades. In the first embodiment, in contrast with the criteria data for each diagnostic item, the skin condition is specified by a level, but in this embodiment, a value which expresses the level is designated as the grade.

Assume that {B1} to {B28} denote the grades concerning the diagnostic items B1 to B28, and the grades of the medium items C1 to C3 and the grade of the skin condition A are expressed with braces { } attached, respectively. Grades {C1}, {C2} and {C3} of the medium items and grade of the skin condition {A} are expressed by equations (1) to (4) of FIG. 9.

Consequently, the central processing unit 13 obtains the grades {B1} to {B28} of the diagnostic items B1 to B28, and the central processing unit can compute grade {A} of the comprehensive skin condition using equations (1) to (4) shown in FIG. 9.

Each coefficient value contained in equations (1) to (4) shown in FIG. 9 varies in accordance with age brackets. This is because the elements which have effects on the visual skin condition vary in accordance with age brackets. For example, in general, the younger age bracket has radiance of skin and resilience of skin, but in this kind of age bracket, coarse skin and creases around the eye may sometimes become highly visible than the older age bracket. That is, for people in their twenties, fine skin texture B9 and creases around the eye B24 have greater contribution to the medium items which are elements of beautiful complexion than other diagnostic items. For the people in their forties, having wrinkles on cheeks makes them suddenly look older and bothers them, but people over 50 feel more concerned about other items than wrinkles on cheeks. When the skin beauty is evaluated, there are differences in areas and items on which attention should be focused in accordance with age brackets in this way. Therefore, in this system, each coefficient value is determined by age and stored.

The coefficient values can be determined, for example, by the following way.

First, assume a data structure as shown in FIG. 10, for which expressions (1) to (4) hold. From measurement data of actual customers for ages scores {B1} to {B28} of diagnostic items are obtained and at the same time, the skin condition by appearance of the customer, that is, the visual skin condition is evaluated to determine grade {A}. Then, a covariance structure analysis, etc. are performed using the visually determined grade {A} and scores {B1} to {B28} of the diagnostic items. Coefficient values b1 to b28 which are degree of contribution of diagnostic items B1 to B28 to each of medium items C1 to C3 as well as c1 to c3 which are degree of contribution of medium items C1 to C3 to grade {A} of the skin condition are computed.

In this way, the coefficient values computed are allowed to have one to one correspondence to the diagnostic items B1 to B28 and medium items C1 to C3 and are stored in the skin judgment criteria database 17.

When the coefficient values are computed, A is rather preferable to have as many combinations as possible of the visual grade {A} with scores {B1} to {B28} based on the measurement data because the coefficient value which conforms to practical values can be obtained. In addition, the evaluation of the visual skin condition could be used by statistically processing the results of evaluation performed by a specialist who is experienced in diagnosing the skin condition or the results of evaluations performed by a large number of inexperienced persons.

The visually evaluated grade {A} used when the coefficient value is determined as described above is the visual grade of the present invention. Only inputting the coefficient value into the central processing unit 13 of this system can compute the grade {A} of the skin condition close to what the central processing unit 13 has visually evaluated.

As described above, the central processing unit 13 analyzes the whole face image data transmitted from the data collection system 1 for each diagnostic item, converts the diagnosis results into scores, and based on the scores, computes grades {C1} to {C3} of the medium item and further computes grade {A} of the skin condition.

When the grade {A} of the customer's skin condition is computed the central processing unit 13 transmits the results to the data collection system 1 via the transmitting and receiving unit 12 and allows the display unit 3 to display the results. However, as the display data to be displayed by the display unit 3, the central processing unit 13 creates display data for displaying the computed grade of each item and the coefficient value that corresponds to the item on the same screen. Examples of the screen displayed by the display data include graphs shown in FIGS. 11 and 12.

FIG. 11 shows the comprehensive skin condition A by two star marks "☆☆" and at the same time grades and coefficient values of medium items C1 to C3 which correspond to the skin condition A. The grade {A} of the skin condition is indicated by a star mark and it is determined that the more the number of stars, the better is the condition and the more beautifully the complexion looks. This grade {A} is a value computed by Eq. (4) of FIG. 9 and in this case, the number of star marks "☆" is determined in accordance with the grade.

In FIG. 11, each of medium items C1, C2, and C3 is taken as abscissa, with the grade of each item as ordinate. The size of grades {C1}, {C2}, and {C3} is expressed by the length of the dotted line, and coefficient values c1, c2, and c3 are expressed by the diameter of circle. However, the center position of each circle is the value of the grade of each of medium items C1 to C3.

Consequently, the grade {A} of the skin condition is the value obtained by multiplying c1, c2, and c3 corresponding to the circle diameter by grades {C1}, {C2}, and {C3} corresponding to the length of each dotted line and by totaling them.

From FIG. 11 like this, it is possible to find out where the factors of the skin condition grade {A} which is rated two star marks "☆☆" are located. In the case of FIG. 11, it is clear that the grade of the color C1 is the lowest and the grade of the irregularity C2 is high. In addition, the coefficient value of the color C1 is greater than the coefficient value of the irregularity C2.

In such case, it is assumed that the comprehensive grade {A} could be efficiently increased by improving the color C1 and raising the grade rather than by improving the irregularity C2 which is presently in the satisfactory level.

In addition, FIG. 12 is a graph that expresses the grade of diagnostic items which compose the color C1, the medium item, taken on abscissa and coefficient values of the diagnostic items B1 to B8 by circles. From his graph, not only advantages and disadvantages of a customer are clarified but also it is possible to grasp which item should be improved to effectively improve the grade of the color C1. For example FIG. 12 indicates that in the diagnostic result of the customer, the grade of dullness of whole face B3 is low and the coefficient value is large. Therefore, it is understood that it would be effective to improve dullness of the whole face to improve the comprehensive skin condition.

When the color C1 of the medium item is chosen by clicking the item name in a state that the grade of the medium item shown in FIG. 11 is displayed on a screen of the display unit 3 on the side of the data collection system 1, the graph shown in FIG. 12 is displayed on the screen. However, this case indicates an example when the color C1 is chosen of the three medium items, but when another medium item is chosen, the graph of the grade of the diagnostic item that corresponds to the medium item is displayed.

In the system of the second embodiment, it is possible to quantitatively evaluate the comprehensive skin condition as the beautiful complexion. In addition, the points to be improved are clarified by indicating grades of medium items and diagnostic items to derive the grade of the comprehensive skin condition, respectively.

Furthermore, displaying the coefficient value of each item enables the customer and the sales person of the cosmetic store to learn the items which can efficiently improve the grade of the skin condition.

The reason why the diagnostic items are classified into medium items, and the grade as well as the coefficient value of the medium item are displayed as shown in FIG. 11 in the second embodiment is that the skin condition can be improved more efficiently.

If no medium item is provided and grades of all the diagnostic items only are displayed, it could be assumed that the diagnostic item with the lowest grade must be unproved.

For example, of all the diagnostic items B1 to B28, the diagnostic item with the lowest score is pimples and pimple marks B15 (see FIG. 8), it is assumed that pimples and pimple marks must be improved for the first time unless grades of the medium items are not known.

However, in actuality, medium items are established and the grades are as shown in FIG. 11. The medium item containing the pimples and pimple marks B15 is the irregularity C2, but as shown in FIG. 11, the grade of the irregularity C2 is high and the grade of the color C1 is lower. This indicates that the grade of each diagnostic item included in the color C1 of the medium item is not the lowest score but the grade is low as a whole.

In addition, the coefficient value c1 of the color C1 is greater than the coefficient value c2 of the irregularity C2. In such a case, it is more effective to raise the grade for the color C1 to raise the grade of the comprehensive skin condition than to improve pimples and pimple marks B15 and raise the grade of the irregularity C2. Specifically, in order to raise the grade of the color C1, it is necessary to implement the skincare methods for improving dullness of whole face B3, dullness of lips B4, brightness B1, and others. However, unless the medium item is established, it is difficult to understand that it is effective to improve the items included in the color C1 to raise the grade of the comprehensive skin condition. In the system of the second embodiment, such thing does not occur and it is easy to clarity effective improvement items.

Furthermore, setting the medium items in such a manner that the diagnostic items to be improved by the similar skincare method are classified into the same medium item can clarify the method of improving the skin condition more efficiently by the grade of the medium item.

FIG. 13 shows an example of medium items based on this kind of skin-care method.

The medium items shown in FIG. 13 are whitening C1, blood circulation C2, moisture retention C3, astringency C4, sebum and horny plug C5, sagging C6, dry wrinkles C7, and aged wrinkles C8. For the whitening C1, as diagnostic items which correspond to the skin condition that varies in accordance with whitening cosmetic methods, brightness B1, color B2, dullness of whole face B3, highly visible spots and freckles B5, and others are classified.

In the same manner, for the blood circulation C2, the diagnostic items of the skin condition which varies in accordance with right and wrong of blood circulation are classified. For the moisture retention C3, diagnostic items of the skin condition which varies in accordance with moisture retention are classified. For the astringency C4, diagnostic items of the skin condition which varies in accordance with the astringent cosmetic methods are classified. For sebum and horny plug C5, the diagnostic items of the skin condition involved with sebum and horny plug are classified. In addition, for sagging C6, dry wrinkles C7, and aged wrinkles C8, diagnostic items related to sagging of skin, dry wrinkles, and aged wrinkles are classified, respectively.

In FIG. 13, the names of diagnostic items classified to each medium item are omitted and symbols only are indicated, but the symbols used here are the same symbols B1 to B28 used in FIG. 8. The coefficient value which is the degree of contribution to the medium item is allowed to have correspondence, respectively, to each diagnostic item.

However, in the classification method shown in FIG. 13, the same diagnostic item corresponds to multiple medium items, in some cases. For example, the dark circles B8 of the diagnostic item is classified into both medium items of whitening C1 and blood circulation C2. This is because the dark circles may be caused by inclination of melanin pigments or by poor blood circulation.

As described above, because the coefficient value of diagnostic items classified into a plurality of medium items indicate the degree of contribution of the diagnostic items to the medium item to which it is classified, the coefficient value may be varied in accordance with the medium items.

In addition, coefficient values have correspondence to the medium items C1 to C8, respectively. When these are aggregated to compute the grade of the skin condition A, coefficient values that correspond to the relevant grades are multiplied and totaled as is the case of the equation shown in FIG. 9.

In addition, the system according to the present invention is allowed to connect a plurality of data collection systems 1 to the data analysis system 11 via communication. This makes it possible to register customer information and face images collected at a plurality of stores to the customer database 15 and face image database 16. In addition, analysis results at the central processing unit 13 can be accumulated, too.

As described above, accumulating customer data and face images collected from the customer throughout the country in the control center enables the people to analyze these data and grasp the regional difference in customer's skin condition.

Because data of a large number of customers which cannot be collected by one store can be accumulated, it is possible to create patterns of face shapes and skin characteristics from the data and to classify the data in accordance with patterns.

Furthermore, if a large volume of data is accumulated and the criteria and the trend of the skin condition for age can be grasped, such data can be utilized for prediction of future face shape and skin condition.

For example, changes of face shape and changes of skin condition can be predicted on the basis of the logics shown in FIGS. 14 and 15.

That is, as is the case with FIG. 14, the whole face image of the customer is enlarged, the skin firmness is estimated from the shape and flow condition of the texture of the mouth, and the customer skin is classified into "firm" type or "not firm" type. In the case of "firm" type, the face shape is classified into "puffy type" and "slender type", and the trend of changes can be specified.

Further, as is the case with FIG. 15, the customer's whole face image is enlarged. The moisture level of the skin is estimated from the degree and flow of the fine texture of the cheek, and the sebum level is estimated from the pore size and horny plug condition as well as age. Then, the skin type is classified into the "supple" type or the "non-supple" type, and the "non-supple" type is further classified into "lots of sebum" type and "little sebum" type, so that the trends of changes of all the types can be specified.

It is also possible to display a predicted future face image on the side of the data collection system 1 if the predicted future face image of the customer future predicted on the basis of the trend of changes specified as above is created and outputted.

Specifically, as shown in FIG. 16, four types of skin condition are created for age, by the presence or absence of "firmness," and by "supple" type and "non-supple" type, and each type is allowed to have correspondence with average face data having average values of the skin condition.

The average face data are values computed for each type classifying the customer data collected in the past in accordance with ages, face type, and absence or presence of firmness. The average values of the diagnostic items are allowed to have correspondence to each type. This kind of average face data is stored in, for example, the skin judgment criteria database 17, etc. on the side of the data analysis system 11 in advance. In implementation, though four types of data are allowed to have correspondence to all the age brackets, part of the data of the "non-supple" type is omitted in FIG. 16.

Whether the skin type is of the "firm" type or "not firm" type cab be identified by determining whether the grade of supple skin B16 of the diagnostic items described in the second embodiment or vitality C3 of the medium item is not less than a reference value set for each age bracket, or less than the reference value. In this case, as shown in FIG. 16, the presence or absence of "firmness" is classified by the vitality level based on the grade of vitality C3. This vitality level indicates that the vitality is lost in order of level 1 to level 8.

In actuality, when the future face image of the customer who comes to the store on the side of the data collection system 1, the customer's whole face image is photographed as is the case of the first and second embodiments. In the data analysis system 11, the skin condition is analyzed and at the same time, the face contour of the customer is analyzed from the whole face image, and the facial form of the customer is identified whether it is the "puffy" type or the "slender" type.

Thereafter, from the skin diagnostic results, presence or absence of firmness is specified based on the grade of vitality C3, and it is determined to which type of the above four types the customer belongs.

For example, in the case of a customer 40 years old, of a "puffy" and "not-firm" type, the customer belongs to type T1 of FIG. 16. This type T1 will become type T2 10 years later.

Therefore, when the face of the customer after 10 years is predicted, the predicted future face image is created by applying the average values concerning the skin condition of type T2 to the face image of the customer. For example, the wrinkle condition that conforms to the grade of forehead wrinkles in the average face is expressed on the customer's face image.

However, this may be modified when the customer has the skin condition far removed from the average face of the type that conforms to her/his age bracket.

For example, the average vitality level of type T1 is 4 but the customer vitality level may be 3. On average, in the case of the above customer at age from 40 to 50, the vitality level is changed to 4 to 5, but the customer has the vitality level 3 at 40. For this reason, when she/he becomes 50 years old, she/he would acquire the vitality level 4 by adding 1, and the skin condition that meets this vitality level should be expressed.

In this way, the central processing unit 13 transmits the created predicted future face image to the data collection system 1 and allows it to be displayed on the display unit 3.

As described above, by accumulating a large volume of data in the data analysis system 11, immeasurable advantages in that various analyses can be performed in still higher accuracy can be achieved.

Furthermore, by separating a large-size processing unit for performing high-precision analysis from the data collection system, the number of stores which can install a small-size data collection system increases, and still greater number of data can be collected to the control center.

In addition, the central processing unit 13 of the data analysis system 11 may choose a skin-care method from the skin-care database 18 or choose products from the product information database 19 in accordance with the skin diagnosis results, and transmit the data to the data collection system 1.

For example, in the skin-care database 18, there is stored a table of various skin-care methods having one-to-one correspondence to reference points that correspond to the diagnostic items. When there is any item which is less than the reference point in the skin condition diagnostic results, the central processing unit 13 extracts the skin-care method that corresponds to the item.

Product information is stored in the product information database 19, and the skin-care method used for the product is stored in each product in such a manner as to have correspondence. For example, skin lotions and serums for supplying the skin with moisture are classified into "moisture" and products for whitening are classified into "whitening." Furthermore, each skin-care method is associated with the diagnostic items and medium items, and products are extracted in accordance with the grade of the item.

For example, when the medium items described in the second embodiment are established from the skin-care viewpoint as shown in FIG. 13, products are allowed to have one to one correspondence to each of medium items and the correspondence table is stored in the product information database 19. In this manner, products which are necessary for improving the skin condition can be automatically extracted depending on the grade of medium items. However, product brands are frequently prepared in the age bracket. In such a case, the correspondence table must be prepared in the age bracket.

This enables the central processing unit 13 to extract the skin-processing method, product information, and other beauty information of the present invention which are suited for the customer's skin condition and to display them on the display unit 3 of the data collection system 1. Even if the shop clerk is an inexperienced newcomer, she/he ban explain the skin-care method which is the best suited for the customer in the same manner as experienced shop clerks.

BRIEF DESCRIPTION OF THE DRAWINGS

FIG. 8 is a table showing a relationship among diagnostic items, medium items, and respective coefficient values according to a second embodiment;

FIG. 9 is an arithmetic expression that computes the grade of medium items and the grade of the skin condition;

FIG. 13 is a table that shows setting examples of medium items;

Figure 16:
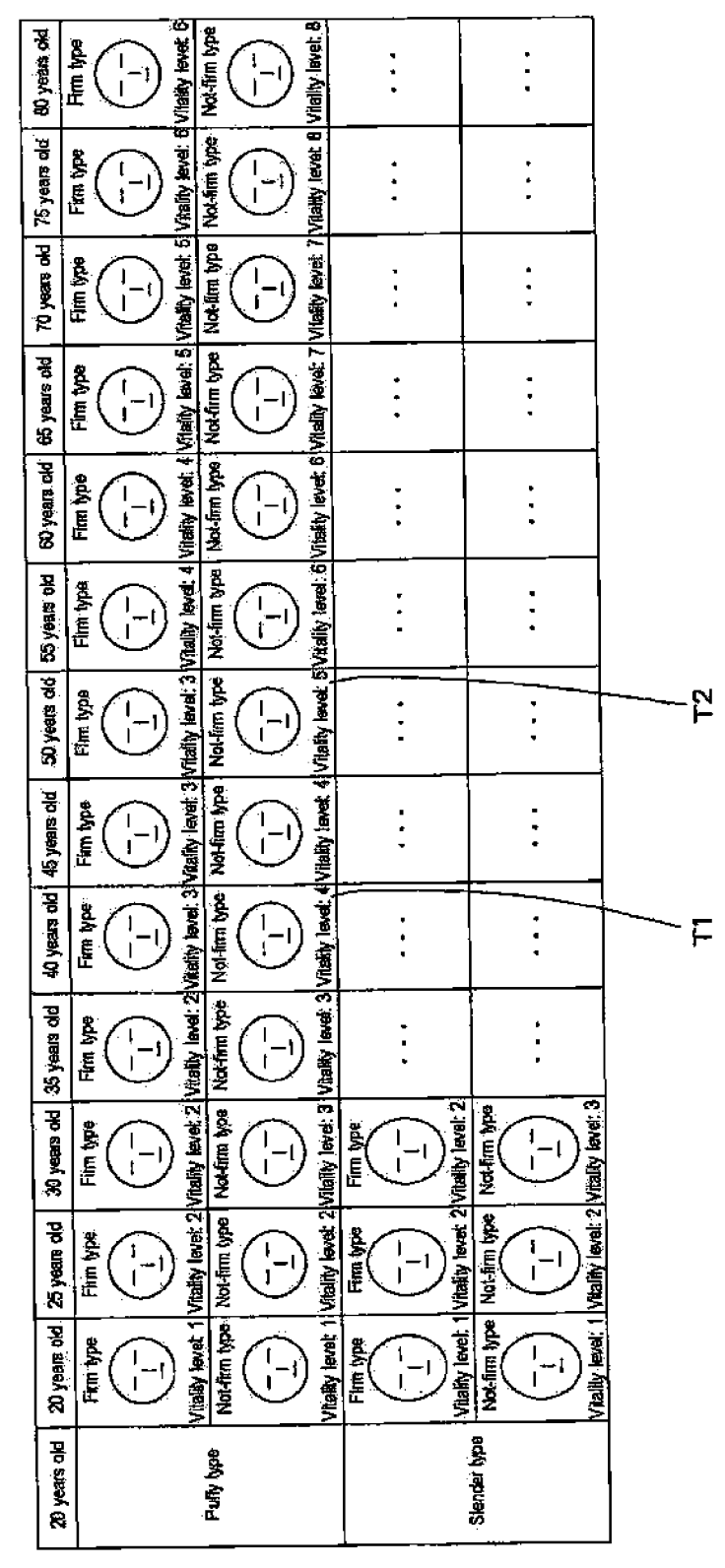

FIG. 16 is an illustration showing an example of reference data of a predicted future face.

EXPLANATION OF REFERENCE NUMERALS

Figure 1:
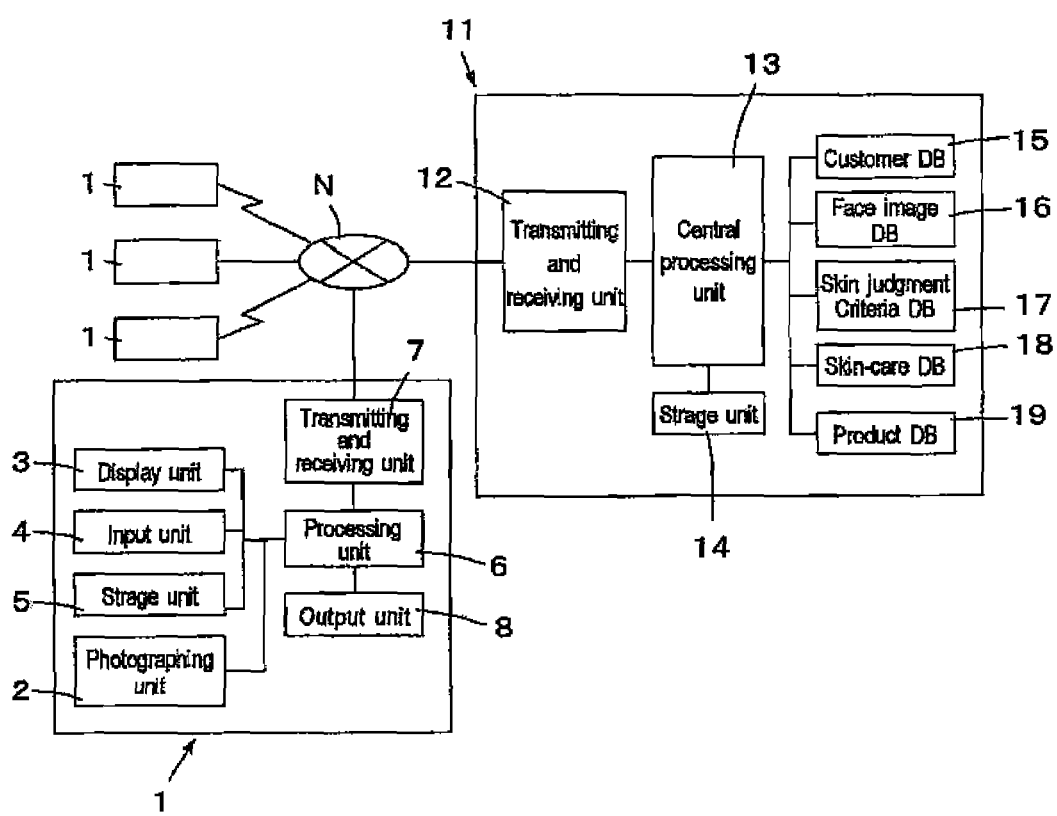
FIG. 1 is a general configuration diagram of a system in a first embodiment of the present invention.
Figure 2:
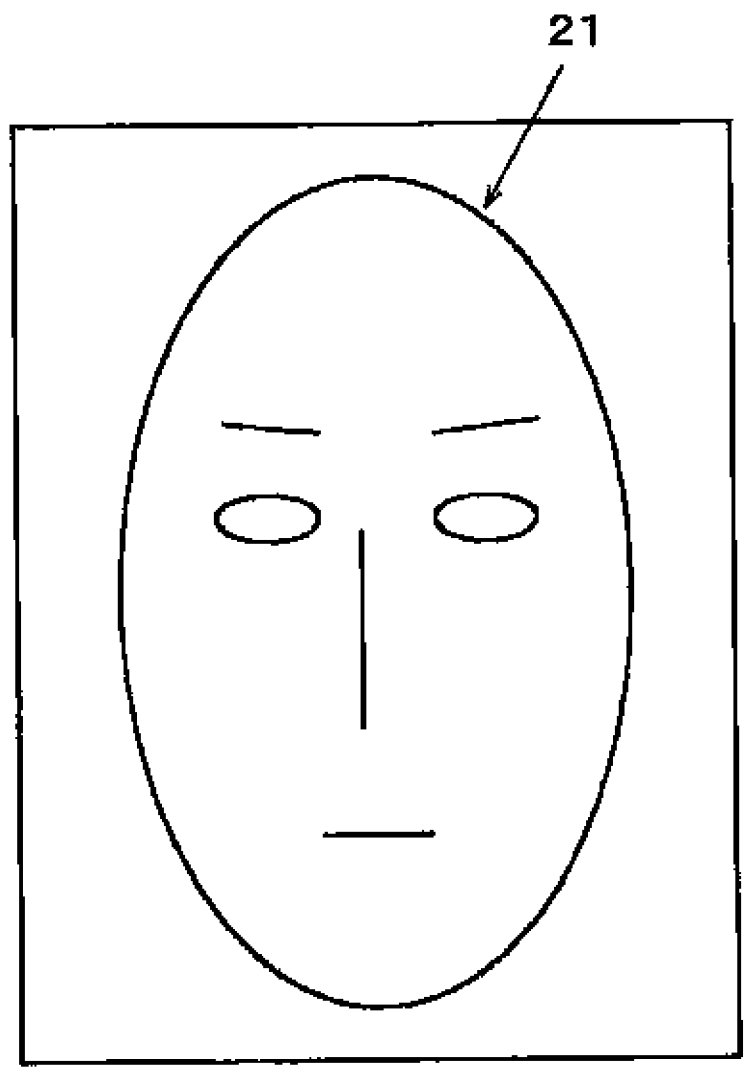
FIG. 2 is a schematic view showing whole face image data subject to analysis of a data analysis system.
Figure 3:
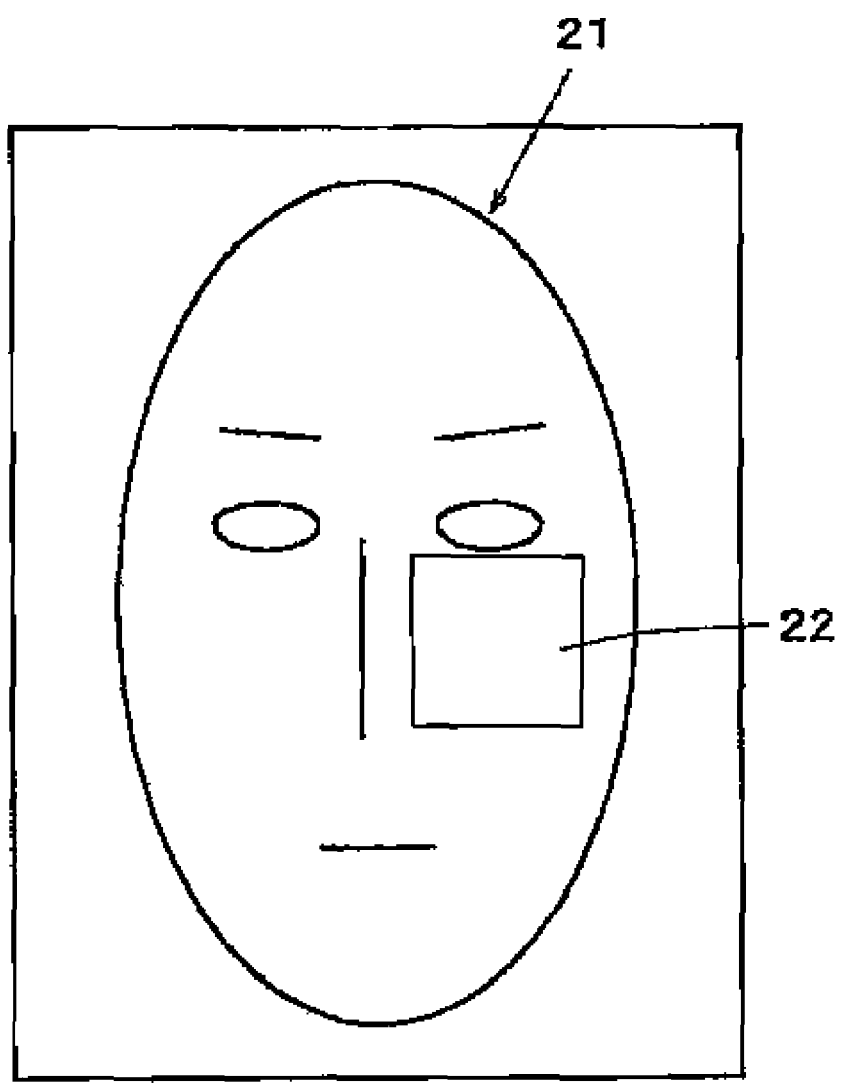
FIG. 3 is an illustration of an analysis portion.
Figure 4:
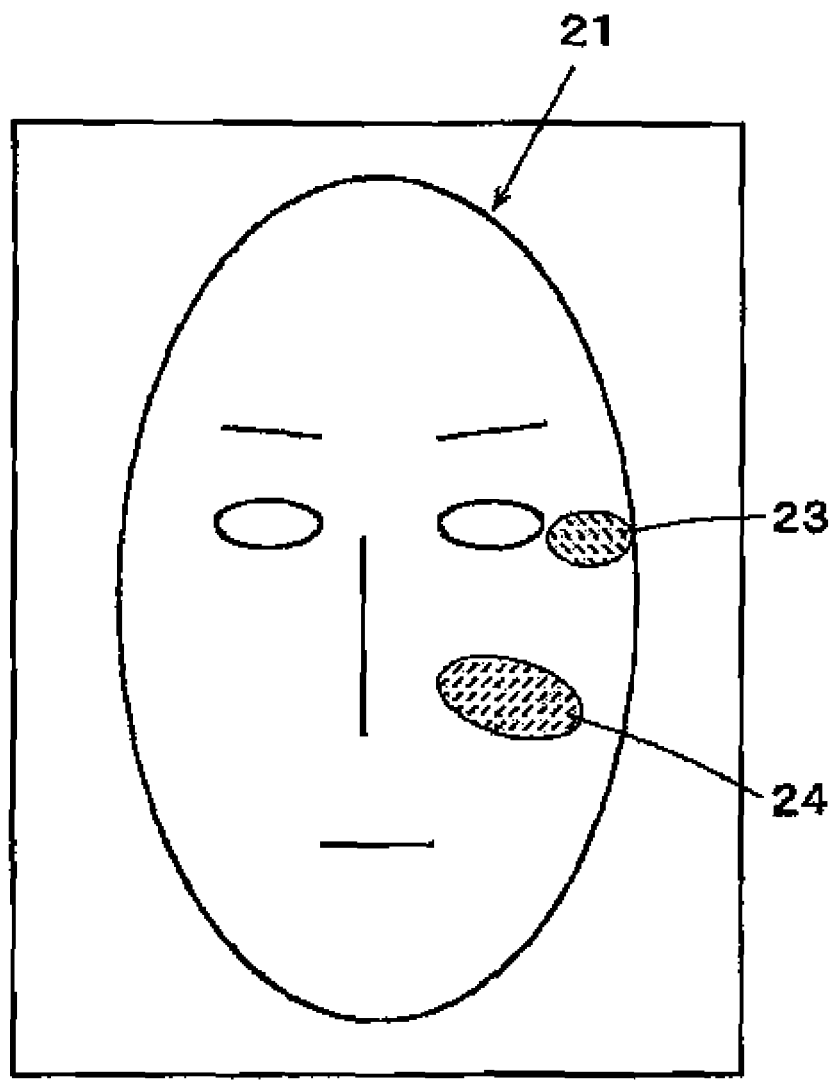
FIG. 4 is an illustration showing the whole face image with diagnostic results reflected.
Figure 5:
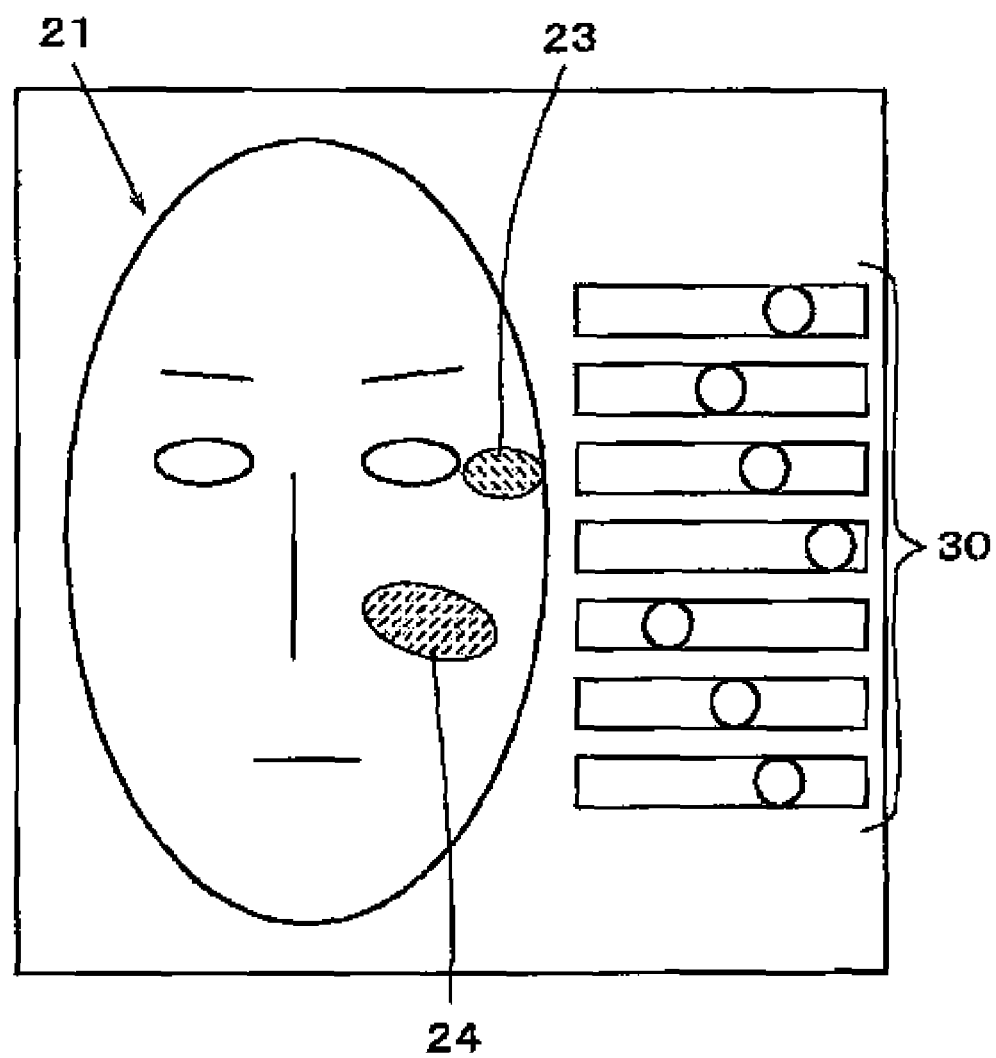
FIG. 5 is an illustration showing a display example of diagnostic results, which is an example to show a skin condition level together with the whole face image.
Figure 6:
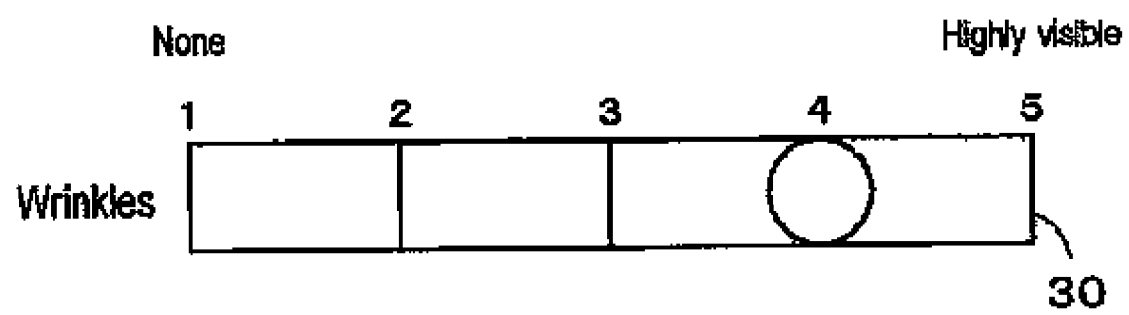
FIG. 6 is a graph showing the level of the skin condition.
Figure 7:
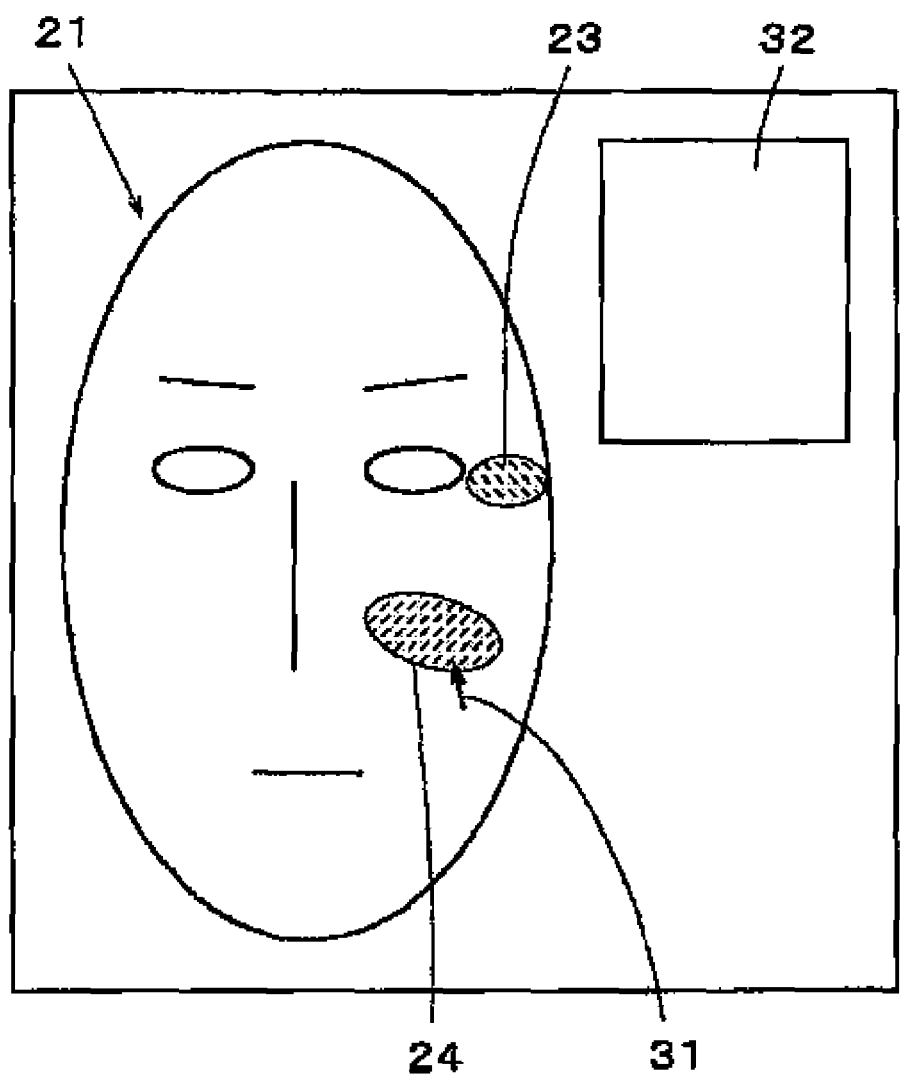
FIG. 7 is an illustration showing a display example of diagnostic results of the first embodiment, which displays an enlarged image together with the whole face image.
Figure 10:
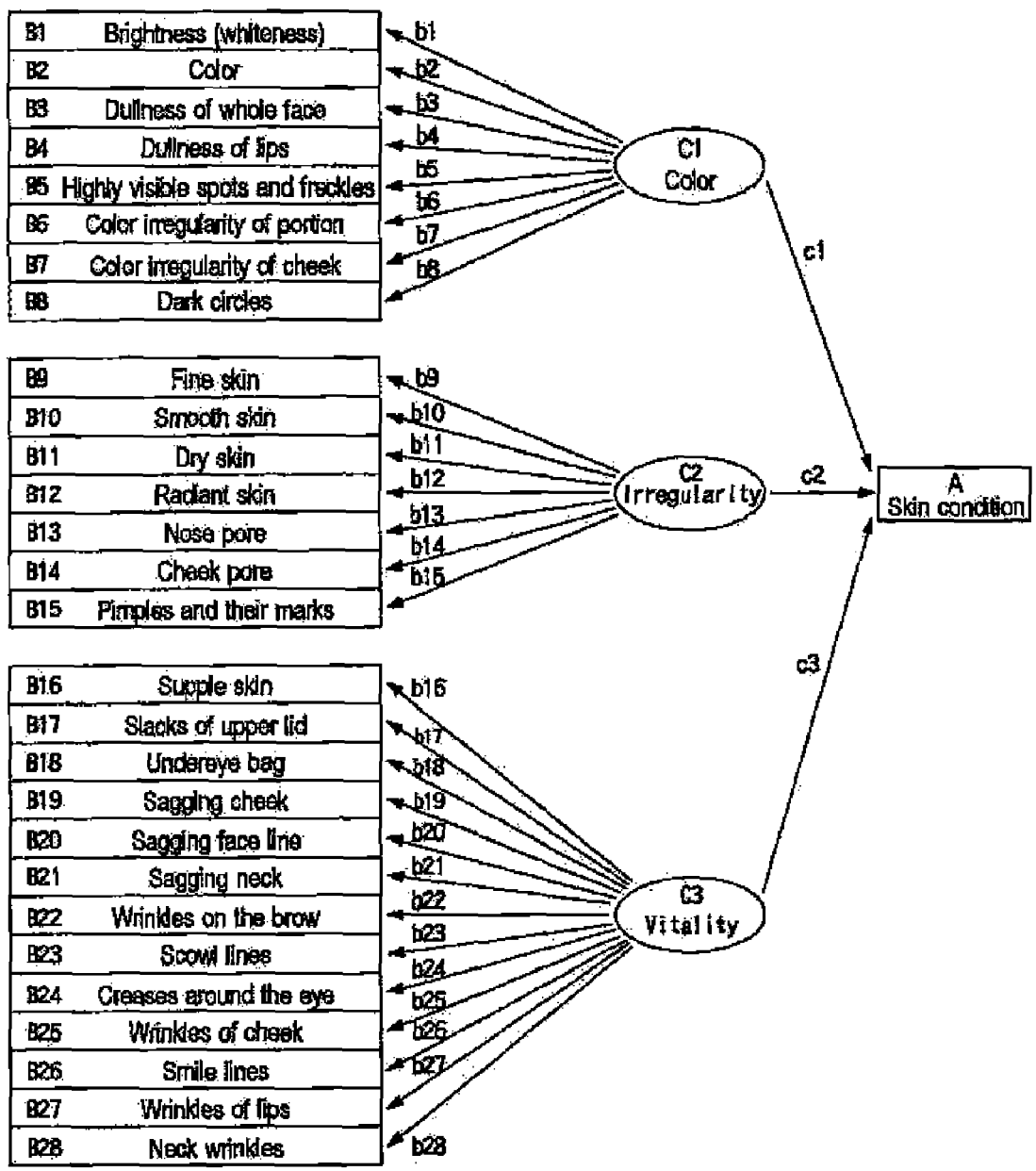
FIG. 10 is an illustration which shows a data structure of the second embodiment.
Figure 11:
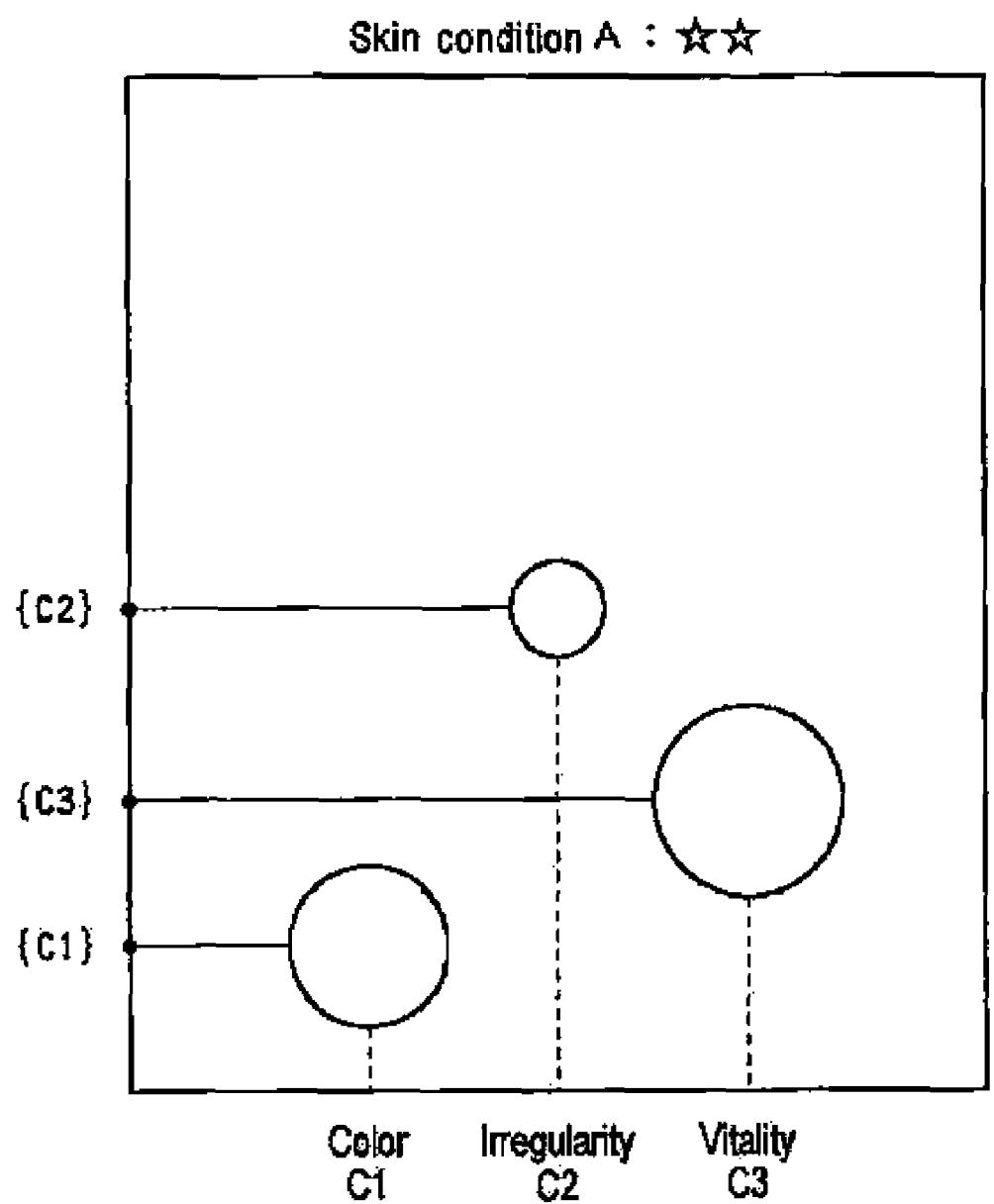
FIG. 11 is a screen that displays diagnostic results of the second embodiment and is an illustration showing the grade of medium items.
Figure 12:
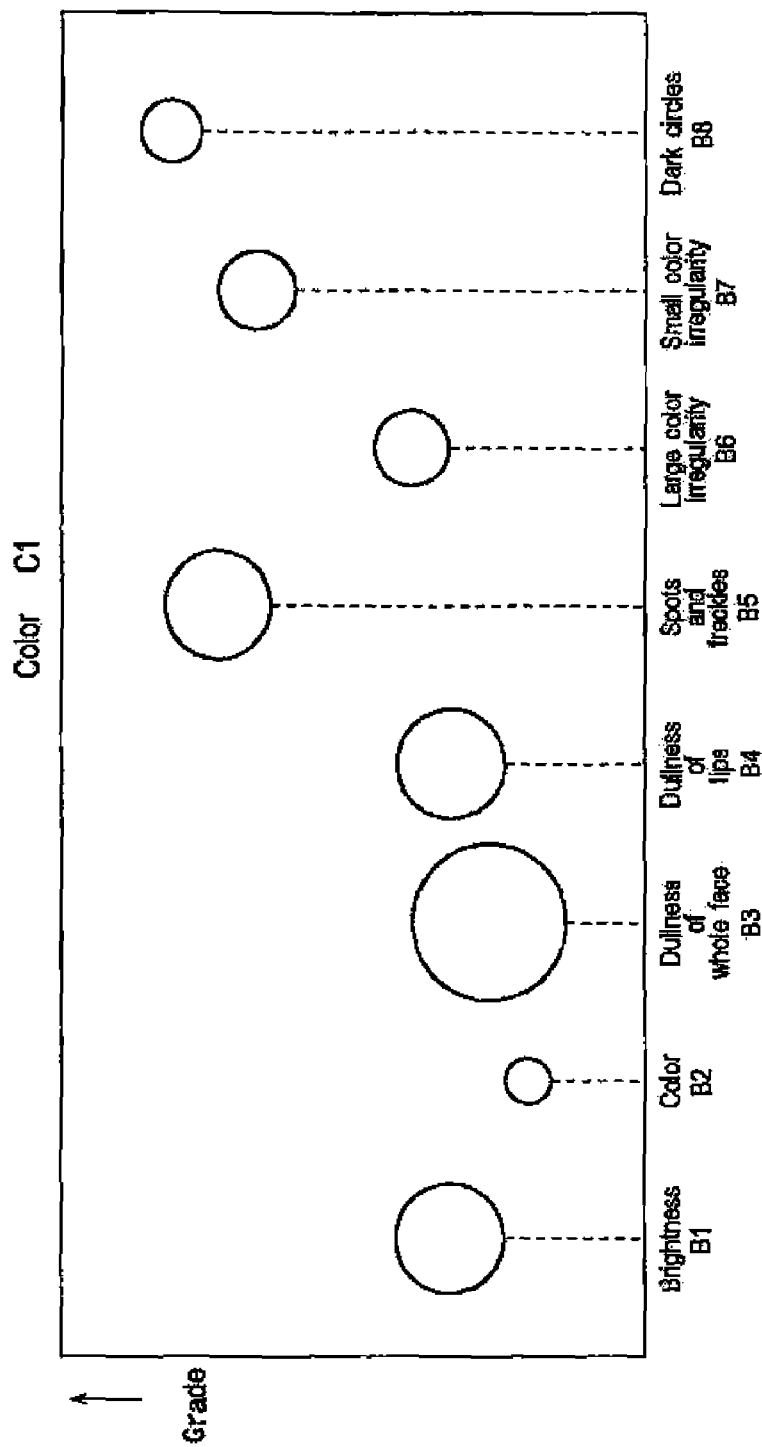
FIG. 12 is a screen that displays diagnostic results of the second embodiment and is an illustration showing the grade of diagnostic items.
Figure 14:
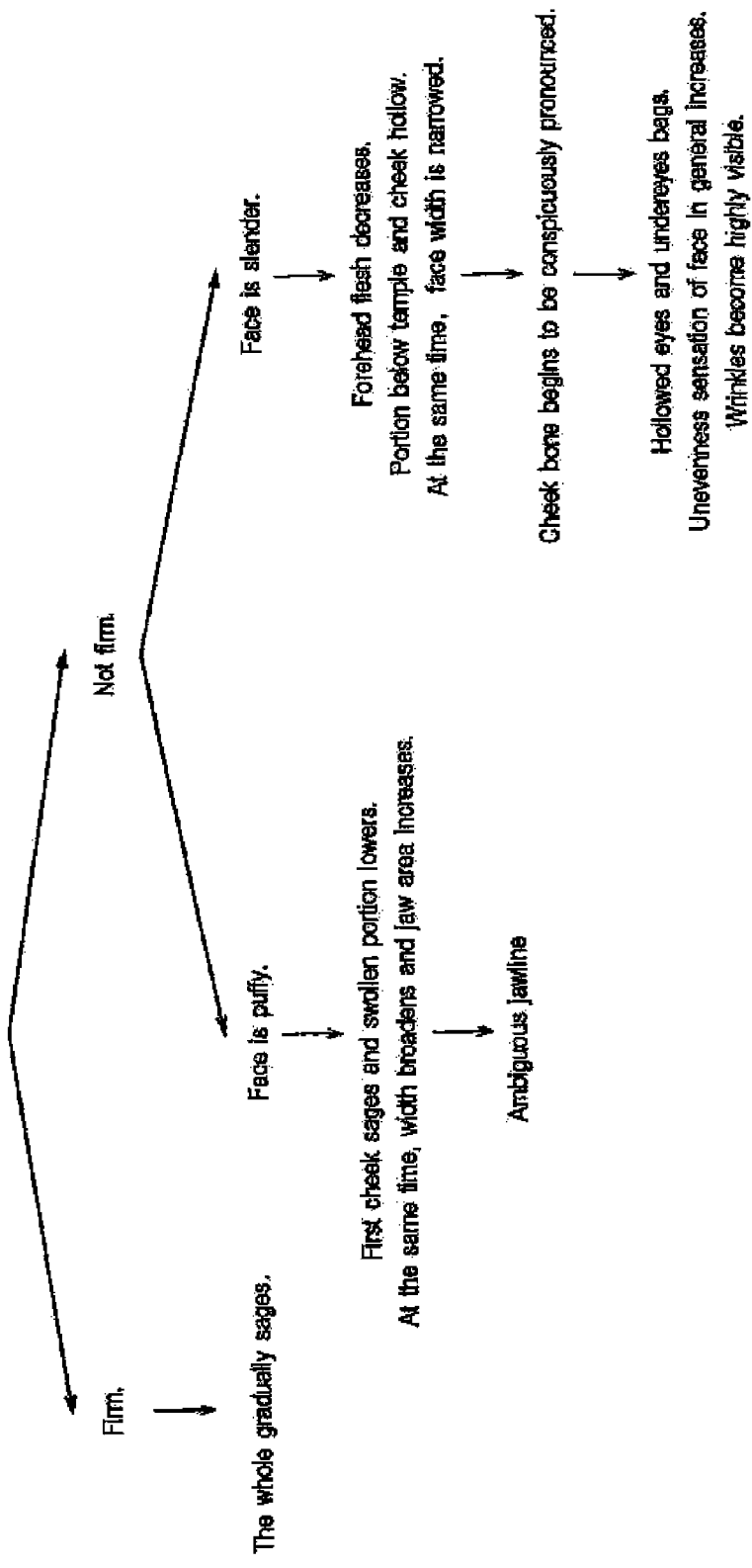
FIG. 14 is an illustration showing an example of aging simulation logic of the face shape.
Figure 15:
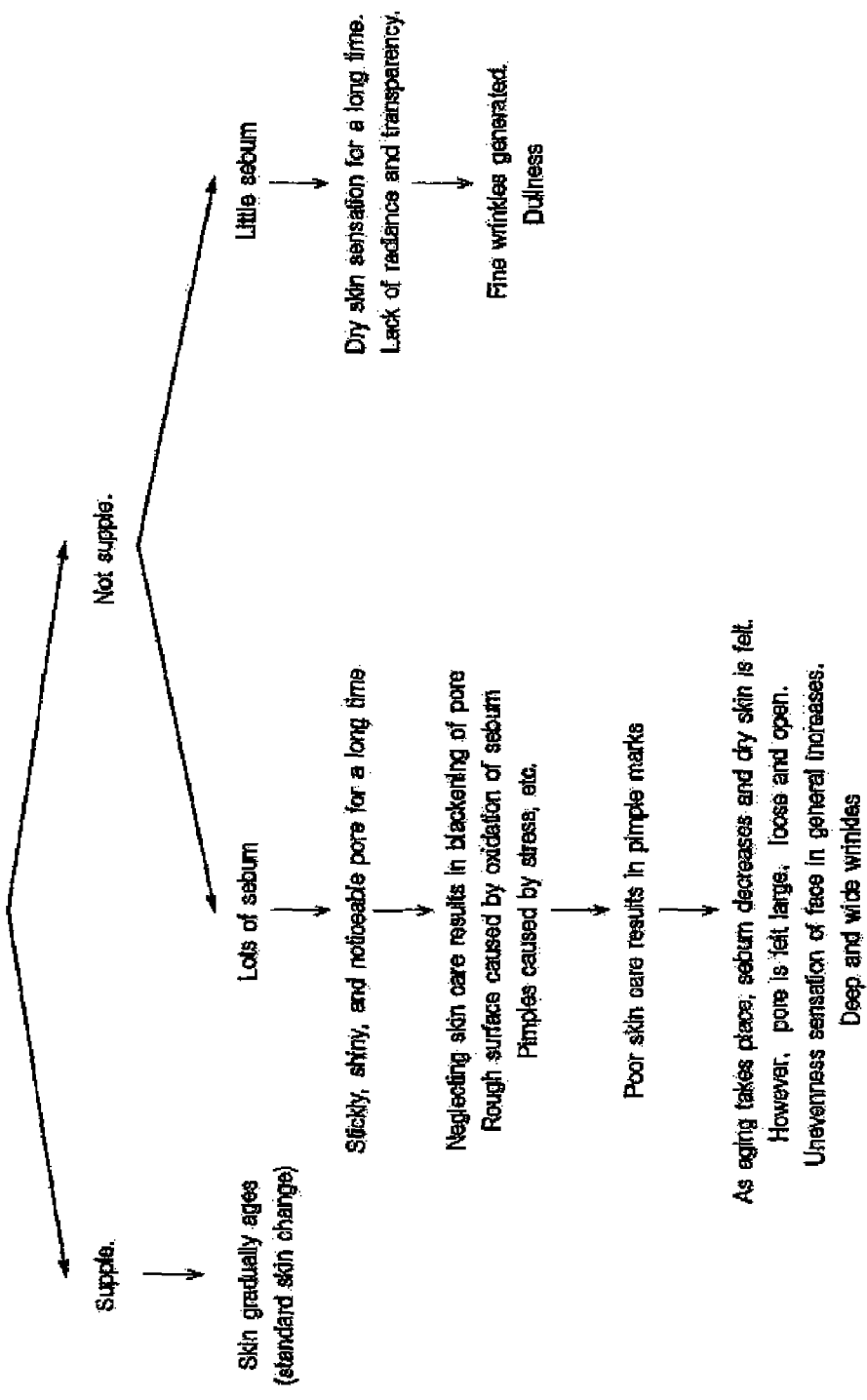
FIG. 15 is an illustration showing an example of aging simulation logic of the skin condition.

1. Data collection system
2. Photographing unit
3. Display unit
4. Processing unit
5. Transmitting and receiving unit
6. Data analysis system
7. Transmitting and receiving unit
8. Central processing unit

The invention claimed is:

1. A skin condition diagnosis system comprising a data collection system and a data analysis system that carries out analysis processing based on data collected by the data collection system, both of which are connected via communication means, characterized in that
the data collection system comprises:
collection-side communication means for transmitting and receiving data to and from the data analysis system;
image capturing means for capturing an ultra-high resolution digital image of such a level as to allow an analysis of a skin texture condition;
collection-side image data compression means for compressing image data by a high-compression method with block noises suppressed; and
collection-side data display means,
the data analysis system comprises:
analysis-side communication means for transmitting and receiving data to and from the data collection means;
data analysis means for analyzing image data;
analysis-side image data compression means for compressing the image data by a high-compression method with block noises suppressed; and
analysis-side data storage means for storing analysis results by the data analysis means,
the image capturing means captures a whole face image of a subject as an ultra-high resolution digital image,
the collection-side image data compression means has a function of compressing the whole face image to create compressed image data and transmitting the data to the data analysis system via the collection-side communication means,
the data analysis means has a function of receiving the compressed image data via the analysis-side communication means, analyzing the skin condition of the subject on the basis of the received compressed image data, creating visual information which reflects the analysis results on the whole face image, and outputting the visual information as a diagnosis result,
the analysis-side image data compression means compresses the diagnosis result outputted from the data analysis means to create compressed image data, and transmits the compressed image data to the data collection system via the analysis-side communication means, and
the collection-side data display means has a function of displaying the diagnosis result transmitted from the analysis-side communication means;
wherein the data analysis system further comprises storage means for storing a plurality of diagnostic items concerning the skin condition, and
the data analysis means has a function of analyzing the skin condition for each of the diagnostic items from whole face image data, computing grades on the basis of the analysis results, and reflecting evaluation results corresponding to the grades to the whole face image; and
wherein the storage means classifies the plurality of diagnostic items into at least two or more kinds of medium items and stores them, and simultaneously stores the medium items and the diagnostic items in such a manner as to be associated with coefficient values, and
the data analysis means aggregates scores of all the diagnostic items, which are obtained by multiplying the computed grade of each diagnosis item by the coefficient value corresponding to the diagnosis item, for each medium item to compute a medium item grade, multiplies the medium item grade by a coefficient value corresponding to the medium item, and aggregates the multiplied scores to compute the grade of the skin condition.

2. The skin condition diagnosis system according to claim 1, wherein the coefficient value is a value computed by analyzing a relationship between a visual grade of the skin condition visually determined and the grade of each diagnosis item computed by the data analysis means.

3. The skin condition diagnosis system according to claim 1, wherein the data analysis means has a function of creating display data for displaying the computed grade and the coefficient value corresponding to the item on the same screen.

4. The skin condition diagnosis system according to any one of claims 1, 2, and 3, wherein the data analysis means executes:
a process for specifying a constituent element of the face from a whole face image received from the data collection system;
a process for specifying a diagnostic items;
a process for specifying a diagnosed portion on the whole face image that conforms to the specified diagnostic item on the basis of the constituent element of the face; and
a process for analyzing image characteristics which appear in accordance with the skin condition that corresponds to the diagnostic item in the diagnosed portion.

5. The skin condition diagnosis system according to claim 1 wherein the medium item is one or more items selected from the group consisting of color, irregularity, and vitality.

6. The skin condition diagnosis system according to claim 5 wherein the medium item is color and the diagnostic item is one or more items selected from the group consisting of whiteness, tint, tone, dullness of whole face, dullness of lips, highly visible spots and freckles, color irregularity of portion, color irregularity of cheek, and dark circles.

7. The skin condition diagnosis system according to claim 5 wherein the medium item is irregularity and the diagnostic item is one or more items selected from the group consisting of fine skin, degree of fine texture, dry skin, radiance of skin, pores on the nose, pores on the cheeks, and pimples and their marks.

8. The skin condition diagnosis system according to claim 5 wherein the medium item is vitality and the diagnostic item is one or more item selected from the group consisting of firmness, slacks of the upper lid, undereye bag, sagging cheek, sagging face line, sagging neck, wrinkles on the brow, scowl lines, creases around the eye, wrinkles of lips, and neck wrinkles.

9. The skin condition diagnosis system according to claim 1 wherein the diagnostic item is one or more item selected from the group consisting of whiteness, tint, tone, dullness of whole face, dullness of lips, highly visible spots and freckles, color irregularity of portion, color irregularity of cheek, dark circles, fine skin, degree of fine texture, dry skin, radiance of skin, pores on the nose, pores on the cheeks, pimples and their marks, firmness, slacks of the upper lid, undereye bag, sagging cheek, sagging face line, sagging neck, wrinkles on the brow, scowl lines, creases around the eye, wrinkles of lips, and neck wrinkles.

10. A skin condition diagnosis system comprising a data collection system and a data analysis system that carries out analysis processing based on data collected by the data collection system, both of which are connected via communication means, characterized in that
the data collection system comprises:
collection-side communication means for transmitting and receiving data to and from the data analysis system;
image capturing means for capturing an ultra-high resolution digital image that allows an analysis of a skin texture condition;
collection-side image data compression means for compressing image data by a high-compression method with block noises suppressed; and
collection-side data display means,
the data analysis system comprises:
analysis-side communication means for transmitting and receiving data to and from the data collection means;
data analysis means for analyzing image data;
analysis-side image data compression means for compressing the image data by a high-compression method with block noises suppressed;
analysis-side data storage means for storing analysis results by the data analysis means; and
change trend storage means for storing trends of changes with time that are compatible with preset skin conditions and face shape patterns,
the image capturing means captures a whole face image of a subject as an ultra-high resolution digital image,
the collection-side image data compression means has a function of compressing the whole face image to create compressed image data and transmitting the data to the data analysis system via the collection-side communication means,
the data analysis means has:
a function of receiving the compressed image data via the analysis-side communication means, analyzing the skin condition of the subject on the basis of the received compressed image data, creating visual information which reflects the analysis results on the whole face image, and outputting the visual information as a diagnosis result;
a function of specifying the pattern from the skin condition and the face shape of the subject, and simultaneously specifying a change trend corresponding to the pattern from the data stored in the change trend storage means; and
a function of predicting the future skin condition and face shape of the subject on the basis of the specified change trend and reflecting the prediction result to the whole face image to output it as a predicted future face image,
the analysis-side image data compression means compresses the predicted future face image outputted from the data analysis means to create compressed image data, and transmits the compressed image data to the data collection system via the analysis-side communication means, and
the collection-side data display means has a function of displaying the predicted future face image transmitted from the analysis-side communication means;
wherein the data analysis system further comprises storage means for storing a plurality of diagnostic items concerning the skin condition, and
the data analysis means has a function of analyzing the skin condition for each of the diagnostic items from whole face image data, computing grades on the basis of the analysis results, and reflecting evaluation results corresponding to the grades to the whole face image; and
wherein the storage means classifies the plurality of diagnostic items into at least two or more kinds of medium items and stores them, and simultaneously stores the medium items and the diagnostic items in such a manner as to be associated with coefficient values, and
the data analysis means aggregates scores of all the diagnostic items, which are obtained by multiplying the computed grade of each diagnosis item by the coefficient value corresponding to the diagnosis item, for each medium item to compute a medium item grade, multiplies the medium item grade by a coefficient value corresponding to the medium item, and aggregates the multiplied scores to compute the grade of the skin condition.

11. The skin condition diagnosis system according to claim 10 wherein the medium item is one or more items selected from the group consisting of color, irregularity, and vitality.

12. The skin condition diagnosis system according to claim 11 wherein the medium item is color and the diagnostic item is one or more items selected from the group consisting of whiteness, tint, tone, dullness of whole face, dullness of lips, highly visible spots and freckles, color irregularity of portion, color irregularity of cheek, and dark circles.

13. The skin condition diagnosis system according to claim 11 wherein the medium item is irregularity and the diagnostic item is one or more items selected from the group consisting of fine skin, degree of fine texture, dry skin, radiance of skin, pores on the nose, pores on the cheeks, and pimples and their marks.

14. The skin condition diagnosis system according to claim 11 wherein the medium item is vitality and the diagnostic item is one or more item selected from the group consisting of firmness, slacks of the upper lid, undereye bag, sagging cheek, sagging face line, sagging neck, wrinkles on the brow, scowl lines, creases around the eye, wrinkles of lips, and neck wrinkles.

15. The skin condition diagnosis system according to claim 10 wherein the diagnostic item is one or more item selected from the group consisting of whiteness, tint, tone, dullness of whole face, dullness of lips, highly visible spots and freckles, color irregularity of portion, color irregularity of cheek, dark circles, fine skin, degree of fine texture, dry skin, radiance of skin, pores on the nose, pores on the cheeks, pimples and their marks, firmness, slacks of the upper lid, undereye bag, sagging cheek, sagging face line, sagging neck, wrinkles on the brow, scowl lines, creases around the eye, wrinkles of lips, and neck wrinkles.

16. A counseling system for beauty, comprising a data collection system and a data analysis system that carries out analysis processing based on data collected by the data collection system, both of which are connected via communication means, characterized in that the data collection system comprises:
collection-side communication means for transmitting and receiving data to and from the data analysis system;
image capturing means for capturing an ultra-high resolution digital image of such a level as to allow an analysis of a skin texture condition;
collection-side image data compression means for compressing image data by a high-compression method with block noises suppressed; and
collection-side data display means,
the data analysis system comprises:
analysis-side communication means for transmitting and receiving data to and from the data collection means;
data analysis means for analyzing image data;
analysis-side image data compression means for compressing the image data by a high-compression method with block noises suppressed;
analysis-side data storage means for storing analysis results by the data analysis means; and
beauty information storage means for storing beauty information such as cosmetic information,
the image capturing means captures a whole face image of a subject as an ultra-high resolution digital image,
the collection-side image data compression means has a function of compressing the whole face image to create compressed image data and transmitting the data to the data analysis system via the collection-side communication means,
the data analysis means has:
a function of receiving the compressed image data via the analysis-side communication means, analyzing the skin condition of the subject on the basis of the received compressed image data, creating visual information which reflects the analysis results on the whole face image, and outputting the visual information as a diagnosis result; and
a function of extracting and outputting beauty information suited for the subject from the beauty information storage means on the basis of the analysis results,
the analysis-side image data compression means compresses the diagnosis result outputted from the data analysis means to create compressed image data, and transmits the compressed image data together with the extracted beauty information to the data collection system via the analysis-side communication means, and
the collection-side data display means has a function of displaying the diagnosis result and beauty information transmitted from the analysis-side communication means;
wherein the data analysis system further comprises storage means for storing a plurality of diagnostic items concerning the skin condition, and
the data analysis means has a function of analyzing the skin condition for each of the diagnostic items from whole face image data, computing grades on the basis of the analysis results, and reflecting evaluation results corresponding to the grades to the whole face image; and
wherein the storage means classifies the plurality of diagnostic items into at least two or more kinds of medium items and stores them, and simultaneously stores the medium items and the diagnostic items in such a manner as to be associated with coefficient values, and
the data analysis means aggregates scores of all the diagnostic items, which are obtained by multiplying the computed grade of each diagnosis item by the coefficient value corresponding to the diagnosis item, for each medium item to compute a medium item grade, multiplies the medium item grade by a coefficient value corresponding to the medium item, and aggregates the multiplied scores to compute the grade of the skin condition.

* * * * *